United States Patent [19]

Sakurai

[11] Patent Number: 5,336,089
[45] Date of Patent: Aug. 9, 1994

[54] DENTAL HANDPIECE
[75] Inventor: Masatoshi Sakurai, Sakado, Japan
[73] Assignee: Promident Manufacturing, Limited, Saitama, Japan
[21] Appl. No.: 75,666
[22] Filed: Jun. 11, 1993
[51] Int. Cl.$^5$ .................. A61C 1/08; A61C 1/05
[52] U.S. Cl. ...................... 433/126; 433/132
[58] Field of Search ............ 433/114, 118, 120, 124, 433/126, 127, 132, 133

[56] References Cited

U.S. PATENT DOCUMENTS

| 2,945,299 | 7/1960 | Fritz | 433/132 |
|---|---|---|---|
| 3,324,553 | 6/1967 | Borden | 433/126 |
| 4,318,695 | 3/1982 | Lieb et al. | 433/132 |
| 4,403,956 | 9/1983 | Nakanishi | 433/126 C |
| 4,403,959 | 9/1983 | Hatakeyama | 433/126 |
| 4,533,324 | 8/1985 | Nakanishi | 433/132 |
| 5,007,832 | 4/1991 | Miller et al. | 433/126 |
| 5,252,067 | 10/1993 | Kakimoto | 433/132 X |

FOREIGN PATENT DOCUMENTS 254458 10/1962 Australia .................. 433/132

Primary Examiner—Gene Mancene
Assistant Examiner—Nicholas D. Lucchesi
Attorney, Agent, or Firm—Koda and Androlia

[57] ABSTRACT

A dental handpiece comprises a handle section and a detachable head section. The head section to which a burr is mounted is made entirely of plastic except for ball bearings so that vibrations are absorbed via its own elasticity. The head section is disposed after use, thus avoiding the secondary infections of, for example, AIDS and hepatitis.

4 Claims, 5 Drawing Sheets

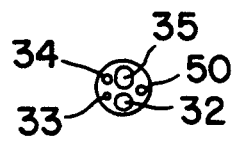
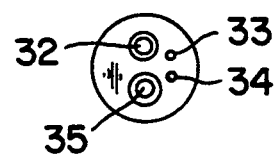
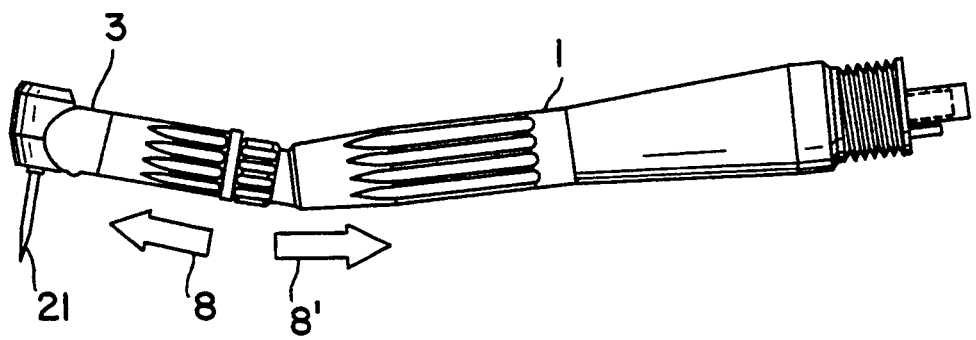
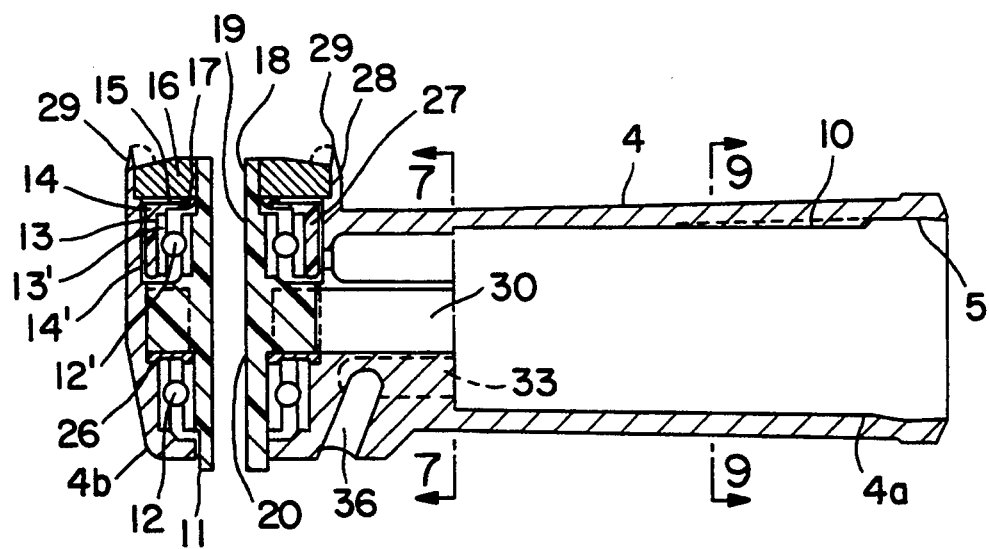

DENTAL HANDPIECE

BACKGROUND OF THE INVENTION

1. Field of the Invention

The present invention relates to a dental handpiece.

2. Prior Art

A conventional handpiece used in dental treatments is a single body equipment. In other words, it comprises a handle and a tip end that are connected together by soldering, screwing, etc., and a driving section that contains a rotor unit for rotating a burr is inserted into the tip end of the handle. The handle and the driving section sections are screwed together by a cap so as to make a single unit.

In the field of dentistry, the secondary infections of AIDS, hepatitis, etc. has increased greatly through the use of dental equipments, and dental handpieces are considered to have a highest risk for such secondary infections.

More specifically, of the dental equipments, pliers and tweezers, for example, can be high heat sterilized without being damaged and can be used repeatedly. However, high heat sterilization is not always a proper cleaning method for the dental handpiece because it is made up of a plurality of high precision mechanical parts including ball bearings and requires a supply of lubricant after the sterilization. In addition, whether or not a sufficient lubricant is put in the handpiece cannot be verified easily.

Furthermore, due to the complex internal structure, a complete sealing is not able to be obtained, and residual dirt can not removed unless the rotor unit which has a turbine, ball bearings, etc. is taken out of the handpiece.

SUMMARY OF THE INVENTION

Accordingly, the object of the present invention is to solve the problems of the existing dental handpiece as described above and to provide a dental handpiece which offers ample protection from the secondary infections of AIDS, hepatitis, etc. seen in the field of dentistry.

In order to accomplish the object, the present invention utilizes a unique structure wherein a handle section and a head section (or a cartridge) that contains a rotational driving source are detachable. In addition, the casing of the head section has a tube portion so that the front end of the handle section is inserted into the tube portion of the head section for accomplishing a secure connection. Furthermore, all parts but the ball bearings which are installed in the head section are made of plastic so that the head section is a disposable molded plastic product.

With the structure described above, the handle section and the head section or the cartridge, which are physically independent, are connected to each other via a snap-in action when used. After the use, they are separated. The handle section is cleaned through high sterilization and high temperature water cleaning processes which are performed repeatedly on the handle section so that the secondary infections AIDS and hepatitis, for example, are prevented. On the other hand, the head section or the cartridge that contains therein a rotor and other parts is disposed after use, thus insuring the sterility, hygiene and safety.

DESCRIPTION OF THE DRAWINGS

FIG. 3 shows a front end of the handle section of the handpiece;

FIG. 4 shows a rear end of the handle section of the handpiece;

FIG. 5 is a side view of the handpiece with the handle section and the head section connected into a single unit;

FIG. 6 is an enlarged sectional view of the head section;

DETAILED DESCRIPTION OF THE INVENTION

Figure 1:
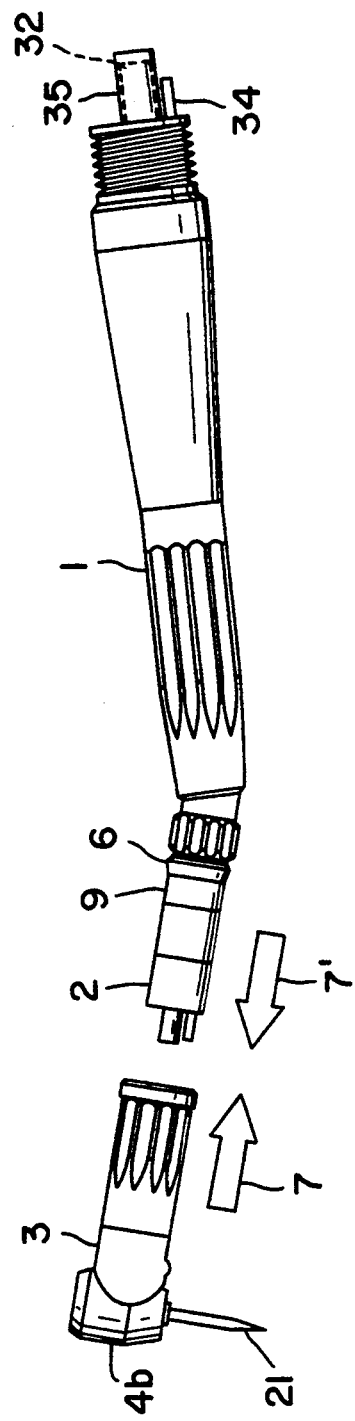
FIG. 1 is a side view of the dental handpiece according to the present invention, the Figure showing the handpiece prior to being connected into single unit.
Figure 2:
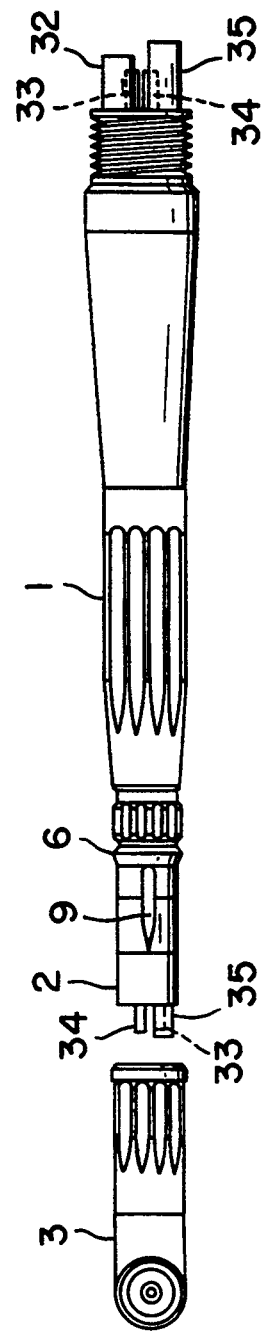
FIG. 2 is a top view thereof.
Figure 7:
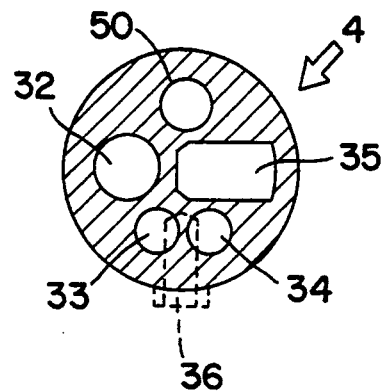
FIG. 7 is a cross section taken along the line 7—7 in FIG. 6.
Figure 8:
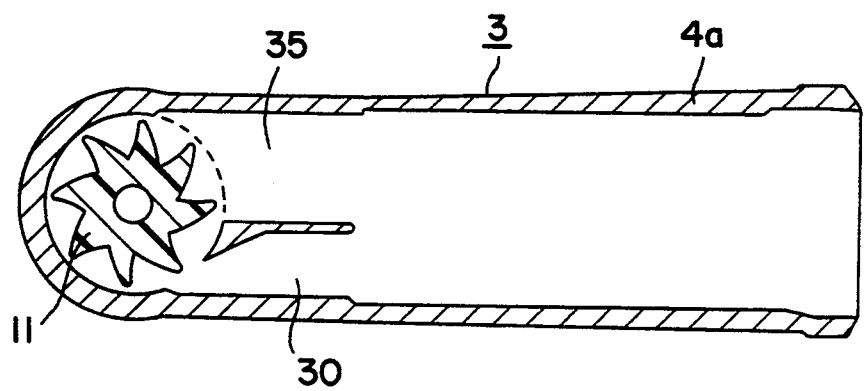
FIG. 8 is a horizontal cross section of the head section, particularly showing the air passage and a turbine rotated by air.
Figure 9:
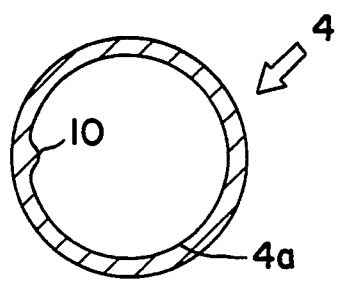
FIG. 9 is a cross section taken along the lines 9—9 in FIG. 6.

The dental handpiece of the present invention will be described below in detail in conjunction with the accompanying drawings.

The handpiece of the present invention comprises a handle section 1 and a head section or a cartridge 3. These two components are separate elements which are connected to and detached from each other.

The handle section 1 is substantially a tube and is made of a material such as a non-rusting metal, heat-resisting resin, etc. that does not change in quality nor shape. Thus, the handle section 1 can be sterilized by high temperature water or high temperature dry heat. The tip portion 2 of the handle section 1 is angled for easier handling in use.

As seen from FIG. 3 that shows the front end of the handle section 1, the handle section 1 contains therein an air supply pipe 32, a water pipe 33, an air pipe 34 and an air exhaust pipe 35. The air supply pipe 32 supplies air into the head section 1 for rotating a turbine (described below), and the water pipe 33 and the air pipe 34 are for jetting out a mixture of air and water. The air exhaust pipe 35 is used for letting out the air that has rotated the turbine.

The front end of the tip portion 2 of the handle section 1 is provided with a gage hole 50. This gage hole 50 has a predetermined diameter so that the tail end portions of burrs may be inserted. Burrs which can be put into the gage hole 50 are determined to be too small in diameter and cannot be used with the dental handpiece because they might come off during the high speed rotation.

The rear end of the handle section 1 is connected to a tube connector (not shown) that is extended from, for example, a dental treatment chair so that air and water are supplied to the handpiece. FIG. 4 shows the rear end of the handle section 1 with the inlets of the pipes opened.

The head section or the cartridge 3 is made of plastic entirely including all the mechanical parts but the ball bearings (described below), so that the head section 3 is manufactured inexpensively and is disposable.

The detail of the head section 3 will be described below in accordance with FIGS. 6 through 11. In these Figures, the reference numeral 21 is a burr which is rotated by the handpiece.

A casing 4, made of plastic, of the head section 3 has at its rear end (right end in FIG. 6) a tube-like or cylindrical sleeve 4a and at its front end a cylindrical frame 4b. The tip portion 2 of the handle section 1 is inserted into the casing 4 so that the handle and head sections 1 and 3 are brought into a single unit. The sleeve 4a, made of plastic, has a shallow groove 5 on the inner circumferential surface so that the sleeve 4a is tightly fitted on the tip portion 2 via its own plastic elasticity.

On the other hand, the front end of the handle section 1 is provided with a ring-shaped projection 6. The projection 6 is formed on the outer circumferential surface near the front end of the handle section 1. The projection 6 is of the size which can tightly fit in the groove 5. Accordingly, when the handle section 1 and the head section 3 are connected, the groove 5 of the head section 3 and the projection 6 of the handle section 1 are tightly engaged with each other via a snap-in fashion. The head section 3 is thus securely mounted to the handle section 1 by a one-touch operation.

Furthermore, a locking groove 9 is formed on the outer surface of the tip portion 2 of the handle section 1. The locking groove 9 extends in the axial direction of the tip portion 2 and lies between the front end and the projection 6 of the tip portion 2. On the other hand, a locking projection 10 is formed on the inner surface of the head section 3 (see FIGS. 6 and 9). The projection 6 is formed in the axial direction of the head section 3 and is about the same size as the locking groove 9. Thus, when the head section 3 is mounted on the handle section 1, the projection 10 engages with the groove 9, and the rotation of the head section 3 in the circumferential direction relative to the handle section 1 is prevented.

The rotational driving source for the burr 21, which is attached to the head section 3, is installed in the cylindrical frame 4b at the front end of the head section 3.

Figure 10:
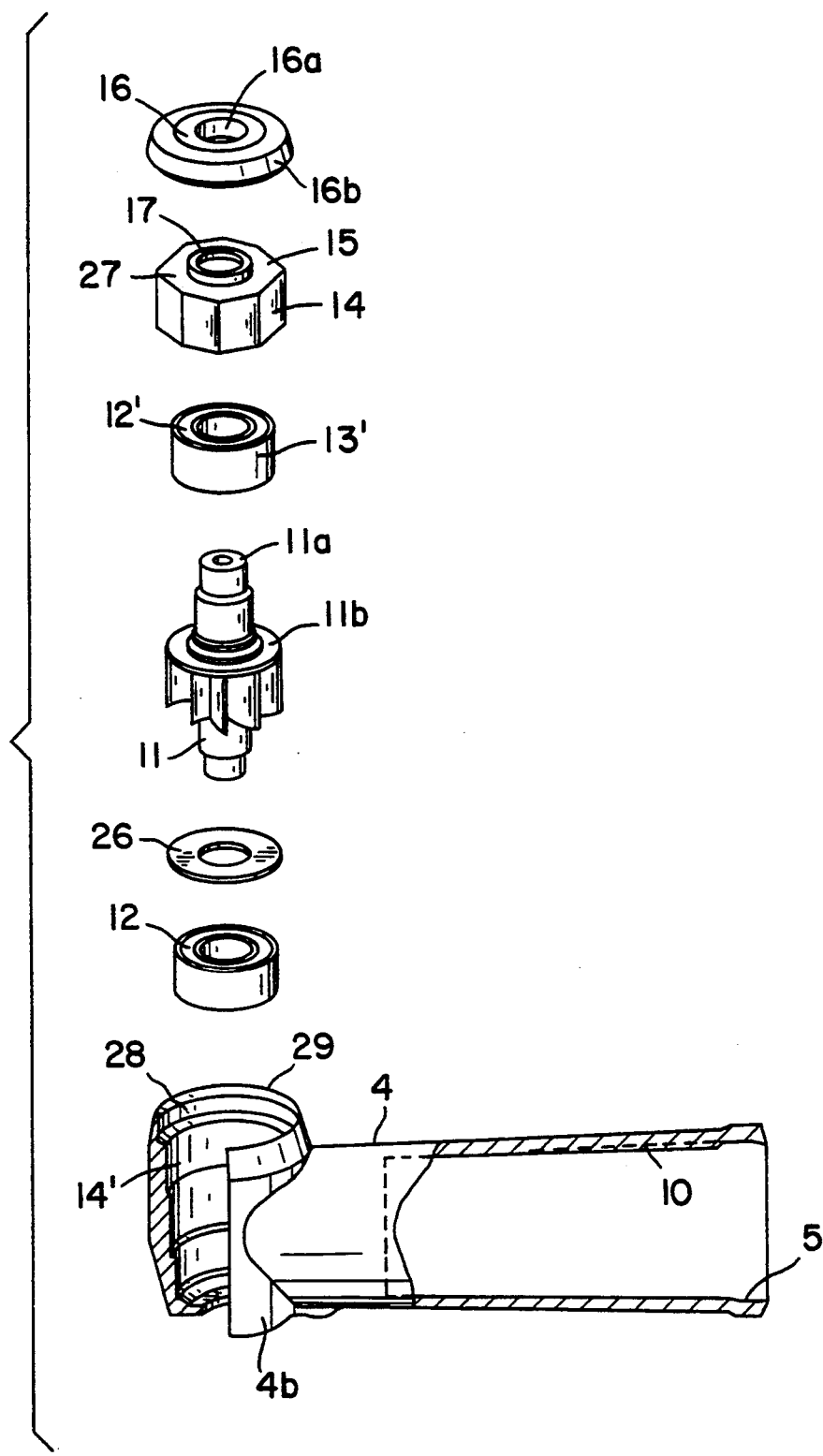
FIG. 10 shows components to be assembled in the head section.

More specifically, the driving source for rotating the burr 21 comprises, as shown in FIGS. 6 and 10, a rotary turbine 11 with its shaft 11a set perpendicular to the axis of the head section 3, and in addition, an upper ball bearing 12' and a preload retainer 27 which are set on the upper side of the turbine 11, and a disk member 26 and a lower ball bearing 12 which are set on the under side of the turbine 11. These elements are mounted on the turbine shaft 11a of the turbine 11. A cap 16 with a center hole 16a and a tapered outer surface 16b is placed on the cylindrical frame 4b.

The turbine 11 has turbine blades, and a circular plate 11b is fixed to the upper ends of the turbine blades so that the expansion of the turbine blades by the centrifugal force is prevented. With the circular plate 11b and the disk member 26 which is mounted on the turbine shaft 11a so as to cover the other (lower) ends of the turbine blades, the end surfaces of the turbine blades are enclosed, and a bucket type turbine is obtained which can efficiently convert the accelerated air into a maximum possible rotational force.

In the structure described above, the inertia which results from the (starting of) rotation of the turbine 11 works so that outer races of the bearings 12 and 12' tend to move in the direction of rotation. In view of this, the outer races of the upper and lower bearings 12 and 12' are positionally secured in the cylindrical frame 4b of the head section 1 so that the balls in the ball bearings 12 and 12' are not hindered from its smooth rotation.

As described above, the ball bearings 12 and 12' are installed on and under the turbine 11. Thus, the ball bearings 12 and 12' are positioned so that they sandwich the blades of the turbine 11.

In this case, because of an R slit (not shown) molded on the inner and the outer races of the ball bearings, an axial space is created which can cause the inner and outer races of the bearings to vibrate in the thrust direction. This vibration needs to be prevented by a certain preload onto the inner and outer races of the bearings 12 and 12' via a spring elasticity which can sterilize the axial space in response to the changes of the radial and axial load which are created when the burr 21 works on a workpiece (tooth). Such an elasticity is provided, in the present invention, by the preload retainer 27 which is made of plastic.

Also, in order to secure the ball bearings so as to function efficiently, the outer races of the bearings 12 and 12' need to be prevented from being rotated by inertia. In other words, the various loads of the thrust and axial directions, which occur at the time of the cutting operation of the burr 21, need to be absorbed. Such an efficient ball bearing function is also obtained by the plastic-made preload retainer 27.

The cap 16 described above is for properly positioning the turbine 11 in the cylindrical frame 4b.

More specifically, the cap 16 with the center hole 16a has a tapered outer surface 16b, and the upper inner surface 28 of the cylindrical frame 4b is shaped into a tapered surface which corresponds to the tapered outer surface 16b of the cap 16. Thus, when the cap 16 is placed, the two tapered surfaces 16b and 28 are snugly fitted together so as not to be loosened. Thus, the cap 16 is securely attached to the cylindrical frame 4b, and the top end of the turbine shaft 11a is brought into the center hole 16a of the cap 16. Accordingly, the turbine 11 can be stable when rotated in the cylindrical frame 4b of the head section 3.

The cylindrical frame 4b has an end flange 29 which is above the tapered surface 28. The end flange 29 is bent inwardly when a heated curling solder is executed to secure the cap 16 on the frame 4b. Below the tapered surface 28, the cylindrical frame 4b has an angled inner surface 14'.

The preload retainer 27 described above is made of plastic and is a hollow nut shape component. It has an angled outer surface 14 and a top end 15. The retainer 27 is designed so that when it is installed inside the frame 4b, a slight space is left between the angled outer surface 14 of the retainer 27 and the angled inner surface 14' of the cylindrical frame 4b so that the retainer 27 is movable in its axial direction.

Figure 11:
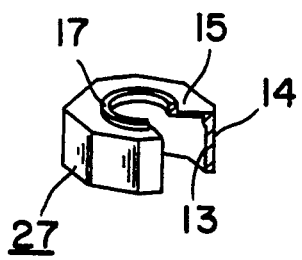
FIG. 11 shows a retainer, one of the components, with a partial cross section.

As illustrated in FIG. 11, the inner surface 13 of the preload retainer 27 is shaped so that it can press fit on the outer race of the upper ball bearing 12'. Thus, the outer race of the bearing 12' is positionally secured. In addition, in order to secure that an axial space is constant, the top end 15, which has an elasticity, of the preload retainer 27 has a rib shape ring 17 which comes into contact with the under surface of the cap 16. The ring 17, when the cap 16 is installed thereon as described above, creates a wavy elastic surface and presses down the outer race of the bearing 12'. Thus, the preload retainer 27 can as a whole move axially by its own spring elasticity to keep the axial direction space inside the cylinder frame 4b constant.

It is necessary that the burr 21 is firmly held even during its high speed rotation, which is provided by the above-described rotational driving source, regardless of its difference in diameter.

In order to obtain such a secure holding of the burr 21, the turbine shaft 11a of the turbine 11, which is made of plastic, has therein a straight portion 20, a stopper portion 18, and a tapered portion 19 as shown in FIG. 6.

The straight portion 20 maintains a straight holding precision of the burr 21. The tapered portion 19 securely holds or chucks the burr 21 via its own plastic elasticity so that the burr 21 does not loosen nor come off of the head section 1 during its high speed rotation.

The stopper portion 18, which is the upper most portion of the inside surface of the turbine shaft 11a, has a smaller diameter than the burrs to be installed. Thus, a burr inserted is stopped at a certain depth and is prevented from sticking out of the upper end of the turbine shaft 11a.

An explanation of the use of the dental handpiece of the present invention will be described below.

When assembled, the handle section 1 and the head section 3 are moved in the directions of arrows 7 and 7', respectively, so that these two parts are made into one piece. The handle section 1 and the head section 3 can be separated from each other manually via a one-touch operation when they are pulled in the direction of arrows 8 and 8' in FIG. 5.

When the two parts are connected as described above, the ring 6 of the handle section 1 and the groove 9 of the head section 3 are engaged, and in addition, the locking projection 10 and the groove 5 are also engaged. Thus, the head section 3 is prevented from not only coming off of the handle section 1 but also from rotating in the circumferential direction.

Next, a burr 21 is inserted into the turbine shaft 11a. Before putting it into the turbine shaft 11a, the shank portion of the burr 21 is put into the gage hole 50. If the burr is easily put in the gaging hole 50, the burr is too small in diameter and cannot be used.

After the determination of the diameter as described above, the burr 21 is inserted into the turbine shaft 11a. When inserted, it is firmly held by the straight portion 20 and the tapered portion 19 inside the turbine shaft 11a. When the turbine 11 is rotated by the air which is supplied through the air supply pipe 32 and then accelerated by an air port 30 (see FIG. 8), the burr 21 is rotated. The air used for rotating the turbine 11 is sent out of the head section 3 via the air exhaust pipe 35.

When the rotating burr 21 is brought into contact with a tooth for cutting, grinding, etc., heat is generated. The heated portion of the tooth and the heated burr 21 are both cooled by the mixture of the water and air. The water and the air are supplied via the water pipe 33 and the air pipe 34 and is jetted out through a mist-outlet 36 opened in the head section 3 (see FIG. 6).

During the treatment that is done with the rotating burr 21, a fluctuating load in the radial and thrust directions acts on the burr 21 and also on the turbine shaft 11a of the turbine 11 depending on the point of the tooth the burr 21 is working on. In this case, it is necessary that the ball bearings 12 and 12' maintain a smooth rolling of their balls. To secure a smooth rolling of the bearing balls relative to the radial and thrust load acting on the ball bearings, it is necessary that the axial space around the bearings 12 and 12' is kept constant via a predetermined preload.

The plastic-made preload retainer 27 maintains the axial space constant. The retainer 27 functions in the following manner:

(1) With its angled outer surface 14, the retainer 27 moves, in response to the excess load that acts at (the start of) the rotational drive and the cutting operation, in the axial direction to prevent the rotation of the outer race of the bearing 12' which is caused by inertia.

(2) With its ring 17 formed on the upper end 15, which provides elasticity and is in contact with the inner surface of the cap 16, the retainer 27 provides a preload with the bearing 12'.

(3) With its outer race retaining portion 13 that can provide pressure so as to prevent the bearing 12' from slipping in the circumferential direction, the retainer 27 positionally secures the outer race of the bearing 12'.

Due to these three functions of the preload retainer 27, the turbine 11 that holds the burr 21 can keep a smooth rotation within the extent of a permitted torque.

The burr 21 is inserted into the turbine shaft 11a and is firmly held by the inner surfaces of the straight portion 20 and the tapered portion 19 of the turbine shaft 11a. The rear or tail end of the burr 21 is stopped by the stopper portion 18 so as not to project out of the turbine shaft 11a.

In the present invention, a turbine assembly, that is obtained by the lower ball bearing 12, the disk member 26, the upper bearing 12' and the preload retainer 27 which are mounted on the turbine shaft 11a of the turbine 11, is installed in the cylindrical frame 4b from the top, and then the cap 16 is placed on the frame 4b. When the cap 16 is installed, the tapered 16b of the cap 16 and the tapered surface 28 of the cylindrical frame 4b are fitted together. After this, the rotation of the turbine 11 is tested.

When the correct rotation of the turbine 11 is confirmed, the end flange 29 is bent inwardly as shown by the broken lines in FIG. 6. Thus, the cap 16 is positionally secured in the frame 4b.

When a defect in the rotation of the burr is found during the test, the cap 16 is removed from the frame 4b. Then, the turbine assembly is taken out of the frame 4b and reinspection is performed to verify, for example, whether or not the steps of assembly have been done correctly.

The test and the inspection described above are performed by applying pressurized air to the blades of the turbine 11. In this case, so as to prevent the cap 16 from being blown out by the pressurized air, the tapered surfaces 16a and 28' of the cap 16 and the frame 4b respectively are fitted together so that the cap 16 is not blown by the air.

After the correct rotation of the turbine 11 is determined, the cap 16 is secured to the frame 4b via a heat curling method.

When the handpiece is used, several different types of burrs are used depending upon the area and condition to be treated.

Accordingly, it is necessary that the burrs are securely held by the turbine shaft even though the diameters are different. It is also necessary that burrs are easily removed from the head section 1. In view of this, a burr is firmly held inside the turbine shaft 11a by being checked via the elasticity of the tapered portion 19.

However, when the burr thus firmly held in the turbine shaft 11a is removed, a considerable amount of torque is required to turn the burr in order to loosen it. It is also necessary that when the attaching and detaching actions of the burr are made, the bearings 12 and 12' are prevented from being damaged.

Figure 12:
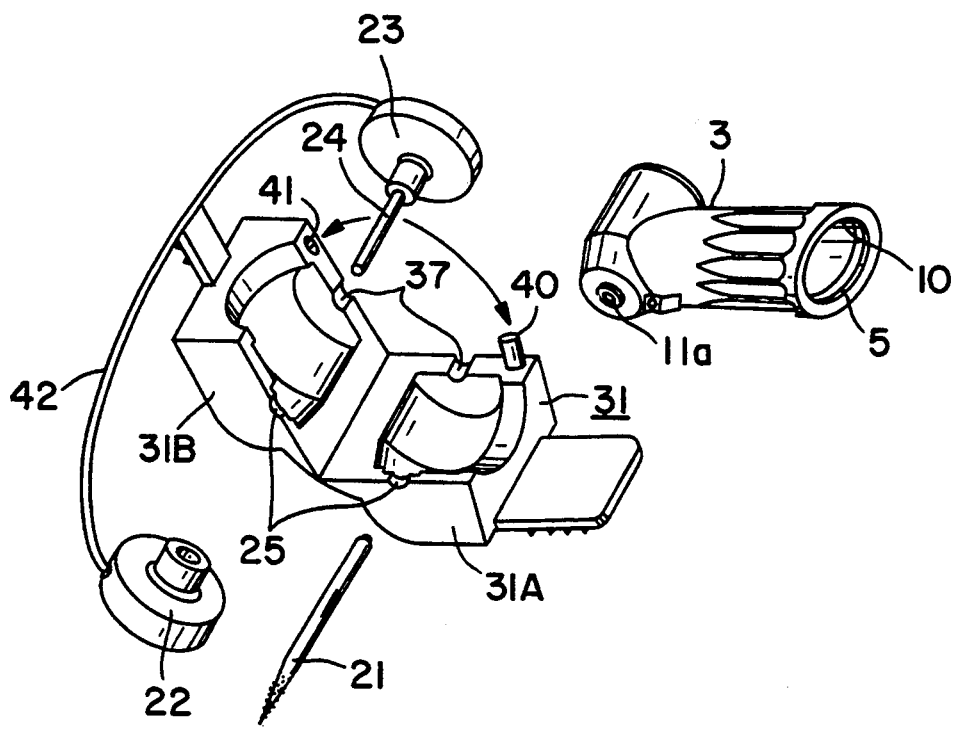
FIG. 12 shows a burr changer for attaching and detaching the burr to and from the head section.

In order to secure a safe and quick mounting and dismounting of the burr, a burr changer 31 as shown in FIG. 12 is used.

The burr changer 31 comprises two hinged sections: the holder base 31A and the holder cover 31B, each having a cavity therein. The two cavities of the two sections form a receptacle which is the same in shape as the outer configuration of the cylinder frame 11a of the head section 3 when the two hinged sections 31A and 31B are brought together and closed.

The holder base 31A has an engagement projection 40, and the holder cover 31B is provided with an engagement recess 41. The projection 40 is brought into the engagement recess 41 when the two sections are closed. Thus, a complete closure of the two sections 31A and 31B is obtained. Each one of the two sections 31A and 31B is provided with a burr guide 25 and a pushing pin guide 37 on opposite ends.

The holder cover 31B is further provided with a burr remover 23, which has a pushing pin 24, and a burr presser 22. The burr remover 23 and the burr presser 22 are provided at both ends of a supporting cord 42 which extends from the holder cover 31B. The burr presser 22 has a tapered surface inside which can comply with the end portions of burrs.

When mounting the burr 21 to the head section 1, the cylindrical frame 4b is placed in the burr changer 31 and the two sections 31A and 31B are closed. When closed, a discrepancy of the two sections is avoided by the projection 40 and the recess 41 which are engaged together, and the cylindrical frame 4b is snugly and tightly held in the receptacle formed by the cavities of the two sections 31A and 31B. Then, the burr 21 is pushed into the turbine shaft 11a via the burr guides 25 and is pushed further by the burr presser 22 until the end of the burr 21 is firmly held by the tapered portion 19 inside the turbine shaft 11a.

When the burr 21 is removed after use from the head section 3, the cylindrical frame 4b with the burr mounted therein is placed in the burr changer 31, and the two sections 31A and 31B are closed. The pushing pin 24 of the burr remover 23 is pushed into the turbine shaft 11a through the pushing pin guides 27 and the center hole 16a of the cap 16, thus forcing out the burr out of the turbine shaft 11a.

With the structure described above, the mounting and dismounting operations of the burr onto and from the head section can be carried out repeatedly without applying any excessive load nor damages to the inner parts of the cylindrical frame 4b including bearings 12 and 12'. In addition, with the burr guides 25 and the push pin guides 37 which help the burr to slide smoothly, any bending of the burr or damage at the tip end of the burr are both efficiently prevented.

As described above in detail, according to the present invention, the handle section and the head section (or the cartridge) are separate parts which can be put into a single body unit with a one-touch action. Accordingly, the handle section can be used repeatedly by performing a high temperature sterilization and a high temperature washing to remove residual infected particles for a complete sterilization. On the other hand, the head section is disposed after use, thus assuring hygiene and safety and preventing the secondary infections of AIDS, hepatitis, etc. in the dentistry.

I claim:

1. A dental handpiece comprising a handle section and a cartridge which are detachable from each other, said cartridge having at one end a cylindrical frame, which contains a rotational driving source for a burr, and at an other end a cylindrical sleeve into which a tip portion of said handle section is inserted; and wherein:

said cylindrical sleeve of said cartridge is provided with a circumferential groove on its inner surface which, via plastic elasticity of said cylindrical sleeve, prevents said tip portion of said handle section from coming off;

said tip portion of said handle section is provided with a ring-shaped projection which engages with said circumferential groove;

a locking groove is provided on an outer surface of said handle section and a locking projection is provided on an inner surface of said cartridge, said groove and projection engaging with each other so as to prevent a circumferential rotation of said cartridge;

said rotational driving source provided in said cylindrical frame of said cartridge is a turbine assembly comprising a lower ball bearing, a ring, an upper ball bearing and a preload retainer which are mounted on a shaft of a turbine, said preload retainer including an outer race retaining part and an elastic top end, an outer race of said upper ball bearing is press fitted to said outer race retaining part and said elastic top end via elasticity of said elastic top end, said retainer presses said upper ball bearing and keeps an axial space constant relative to a fluctuating load applied to said upper ball bearing;

a shaft of said turbine comprises a hollow straight interior portion for holding said burr straight, a stopper portion of a smaller diameter than that of said burr for preventing said burr from sticking out of said turbine shaft, and a tapered portion provided between said straight portion and said stopper portion for holding said burr; and said cylindrical frame of said cartridge is provided with a tapered inner surface on which a tapered outer surface of a cap is fitted.

2. A dental handpiece according to claim 1, wherein said handle section is provided with a gage hole, said gage hole for inserting a tail end of a burr therein to determine capability of use of said burr with the handpiece.

3. A dental handpiece comprising a handle section and a cartridge which are detachable from each other, said cartridge having at one end a cylindrical frame, which contains a rotational driving source for a burr, and at an other end a cylindrical sleeve into which a tip portion of said handle section is inserted; and:

said cylindrical sleeve of said cartridge is provided with a circumferential groove on its inner surface which, via plastic elasticity of said cylindrical sleeve, prevents said tip portion of said handle section from coming off;

said tip portion of said handle section is provided with a ring shaped projection which engages with said circumferential groove;

a locking groove is provide on an outer surface of said handle section and a locking projection is provided on an inner surface of said cylindrical sleeve, said locking groove and projection engaging with each other so as to prevent a circumferential rotation of said cartridge;

said rotational driving source provided in said cylindrical frame of said cartridge is a turbine assembly comprising a lower ball bearing, a ring, an upper ball bearing and a preload retainer which are mounted on a shaft of a turbine, said preload retainer including an outer race retaining part and an elastic top end, an outer race of said upper ball bearing is press fitted to said outer race retaining part and said elastic top end, via elasticity of said elastic top end, said retainer presses said upper ball bearing and keeps an axial space constant relative to a fluctuating load applied to said upper ball bearing;

said cartridge except for said upper and lower ball bearings is made of plastic;

a shaft of said turbine comprises a hollow straight interior portion for holding said burr straight, a stopper portion of a smaller diameter than that of said burr for preventing said burr from sticking out of said turbine shaft, and tapered portion provided between said straight portion and said stopper portion for holding said burr;

said cylindrical frame of said cartridge is provided with a tapered inner surface in which a tapered outer surface of a cap is fitted; and said handle section is provided with a gage hole, said gage hole for inserting a tail end of a burr therein to determine capability of use of said burr with the handpiece.

4. A dental handpiece comprising a handle section and a cartridge which are detachable from each other, said cartridge having at one end a cylindrical frame, which contains a rotational driving source for a burr, and at an other end a cylindrical sleeve into which a tip portion of said handle section is inserted; and wherein said handle section is provided with a gage hole, said gage hole comprising means allowing insertion of a tail end of a burr therein said gage hole having a predetermined diameter which determines of use of said burr with the handpiece, when said burr is in said gage hole.

* * * * *